United States Patent [19]

Junino et al.

[11] Patent Number: 5,085,860
[45] Date of Patent: Feb. 4, 1992

[54] REDUCING COMPOSITION FOR THE PERMANENT DEFORMATION OF HAIR CONTAINING AS A REDUCING AGENT, AN AMINO MERCAPTOALKYLAMIDE OR A SALT THEREOF

[75] Inventors: Alex Junino, Livry Gargan; Gérard Malle, Villiers S/Morin, both of France

[73] Assignee: L'oreal, Paris, France

[21] Appl. No.: 615,626

[22] Filed: Nov. 19, 1990

[30] Foreign Application Priority Data

Nov. 20, 1989 [FR] France .................. 89 15182

[51] Int. Cl.$^5$ .................. A61K 7/09; A45D 7/04
[52] U.S. Cl. .................. 424/72; 424/71; 132/204; 132/205; 132/209
[58] Field of Search .................. 424/72, 71; 132/204, 132/205, 209

[56] References Cited

U.S. PATENT DOCUMENTS

| | | | |
|---|---|---|---|
| 2,540,494 | 2/1951 | Schwarz | 424/72 X |
| 2,751,409 | 6/1956 | Kuhn et al. | 424/71 X |
| 3,768,490 | 10/1973 | Kalopissis et al. | 132/203 |
| 4,851,215 | 7/1989 | Smith et al. | 424/72 |
| 4,956,175 | 9/1990 | Maignan et al. | 424/72 |

OTHER PUBLICATIONS

Patent Abstracts of Japan, vol. 6, No. 214 (C-131)[1092], Oct. 27, 1982 and JP-A-57 118 556.

Patent Abstracts of Japan, vol. 4, No. 34 (C-3)[516], Mar. 22, 1980 and JP-A-55 7222.

Patent Abstracts of Japan, vol. 7, No. 131 (C-169) [1276], Jun. 8, 1983 and JP-A-58 46 063.

*Primary Examiner*—Thurman K Page
*Assistant Examiner*—Susan S. Rucker
*Attorney, Agent, or Firm*—Cushman, Darby & Cushman

[57] ABSTRACT

A cosmetic composition for the first stage of a permanent deformation of the hair contains, in a cosmetically acceptable vehicle, as a reducing agent, an amino mercaptoalkylamide having the formula $$HS-A-NH-CO-\underset{R_1}{\underset{|}{CH}}-(CH_2)_m-NH_2 \qquad (I)$$

wherein
A represents the divalent radical, $-(CH_2)_n-$ wherein n is a whole number ranging from 2 to 5, or the divalent radical $-(CH_2)-O-(CH_2)_2-$, m is 0 or a whole number ranging from 1 to 4, and (i) when m is 0, $R_2$ represents hydrogen methyl, ethyl, isopropyl, isobutyl, 2-methyl butyl, benzyl, 4-amino butyl, 3-guanidino propyl, 2-methylthio ethyl, carboxymethyl or 2-carboxyethyl, and (ii) when m is a whole number from 1 to 4, $R_1$ represents hydrogen or lower alkyl having 1-5 carbon atoms, and the salts of the compound of formula I.

20 Claims, No Drawings

REDUCING COMPOSITION FOR THE PERMANENT DEFORMATION OF HAIR CONTAINING AS A REDUCING AGENT, AN AMINO MERCAPTOALKYLAMIDE OR A SALT THEREOF

The present invention relates to a reducing composition, for use in the first stage of an operation for the permanent deformation of hair, said composition containing, as a reducing agent, an amino mercaptoalkylamide or one of its cosmetically acceptable salts, and its use in a process for the permanent deformation of hair.

The procedures for effecting the permanent deformation of hair comprise, in a first stage, effecting the opening of the disulfide bonds of keratin (cystine) using a composition containing a reducing agent (reduction stage) then, preferably after having rinsed the hair, reconstituting in a second stage the said disulfide bonds by applying, on the hair under tension, an oxidizing composition (oxidation stage which is also called a fixation stage) so as to impart to the hair the desired form or shape. These procedures permit indifferently to effect either a waving of the hair or a straightening of the hair.

Compositions for effecting the first stage of a permanent operation are generally provided in the form of lotions, creams, gels or powders to be diluted in a liquid support, and containing, preferably, as a reducing agent, a mercaptan.

Among the latter, those presently employed are thioglycolic acid and thiolactic acid or a mixture of these acids as well as their esters, for example, glycerol or glycol monothioglycolate.

These reducing agents are particularly effective to reduce the disulfide bonds of keratin. Thioglycolic acid, in particular, is considered the product of choice in permanent deformation operations since it provides an amount of reduction of about 50%.

These reducing agents exhibit, however, a major disadvantage because they give off unpleasant odors.

With a view to remedy this, perfume is generally employed so as to mask these odors.

After significant research efforts, it has now been found, in a quite unexpected and surprising manner, that by using a new family of amino mercaptoalkylamides or their cosmetically acceptable salts, it is possible to overcome the disadvantages experienced with presently employed reducing agents.

The reducing agents of the compositions, in accordance with the present invention, exhibit not only the advantage of being practically free of odor but they also provide a yield, a liveliness and a beauty of curling greater than that obtained in accordance with present operations using, for example, thioglycolic acid.

The present invention thus relates to, as a new industrial product, a cosmetic composition for the first stage of an operation for the permanent deformation of hair, containing in a cosmetically acceptable vehicle, as a reducing agent, at least one amino mercaptoalkylamide having the following general formula (I):

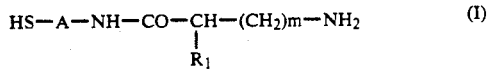

wherein

A represents the divalent radical, $-(CH_2)_n-$, wherein n is a whole number between 2 and 5, or the divalent radical, $-(CH_2)_2-O-(CH_2)_2-$, m is 0 or a whole number between 1 and 4, (i) when m is 0, $R_1$ represents hydrogen, methyl, ethyl, isopropyl, isobutyl, 2-methyl butyl, benzyl, 4-amino butyl, 3-guanidino propyl, 2-methylthio ethyl, carboxymethyl or 2-carboxyethyl, (ii) when m is a whole number from 1 to 4, $R_1$ represents hydrogen or linear or branched lower alkyl having 1-5 carbon atoms, and the salts of said compound of formula I.

Among the cosmetically acceptable salts of the compounds of formula I those particularly preferred are the hydrochlorides, hydrobromides, citrates and oxalates.

By lower alkyl having 1-5 carbon atoms is meant methyl, ethyl, propyl, isopropyl, butyl, isobutyl, 2-methyl butyl and pentyl.

Representative preferred compounds of general formula (I) include principally:

3-amino N-(2-mercaptoethyl) propionamide or aletheine,
2-amino N-(2-mercaptoethyl) acetamide,
2-amino N-(3-mercaptopropyl) acetamide,
2-amino N-(5-mercaptopentyl) acetamide,
2-amino N-[2'-(2-mercaptoethoxy) ethyl] acetamide,
2-amino N-(2-mercaptoethyl) propionamide,
2-amino N-(3-mercaptopropyl) propionamide,
2-amino N-(5-mercaptopentyl) propionamide,
2-amino N-[(2-mercapto-2'-ethoxy) ethyl] propionamide,
3-amino N-(3-mercaptopropyl) propionamide,
3-amino N-(5-mercaptopentyl) propionamide,
3-amino N-[2'-(2-mercaptoethoxy) ethyl] propionamide
2-amino N-(2-mercaptoethyl)-3-methyl butanamide,
2-amino N-(2-mercaptoethyl)-4-methyl pentanamide,
α-amino N-(2-mercaptoethyl) hydrocinnamide,
4-amino-5-[(2-mercaptoethyl) amino]-5-oxo pentanoic acid,
4-amino N-(2-mercaptoethyl) butanamide,
4-amino N-(3-mercaptopropyl) butanamide,
6-amino N-(5-mercaptopentyl) butanamide,
4-amino [N-2'-(2-mercaptoethoxy) ethyl] butanamide and
6-amino N-(2-mercaptoethyl) hexanamide, as well as their hydrochlorides.

The compounds of general formula (I), of which certain ones are known, are prepared in accordance with known methods, mentioned hereafter, which depend upon different substituents, initial reactants employed and their ease of use.

The compounds in accordance with the invention can principally be prepared from the intermediate thioesters of general formula (II):

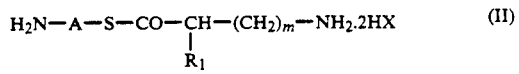

wherein

A, $R_1$ and m have the same meanings as those above for general formula (I), and, X is Cl or Br.

These thioesters are obtained, either by condensation of an aminothiol on an amino acid acid halide such as described, for example, by Th. Wieland et al, Justus Liebigs Annalen der Chemie, 576, 20, (1952), or by hydrolysis of a substituted thiazoline, this being obtained by reaction of an aminonitrile with an aminothiol such as cysteamine, as described in Japanese patent applications 66/22389, 75/62931 and 75/62932 of Daichi Segaku Company.

The thioesters of general formula II are rearranged into amino mercaptoalkylamides of general formula I by treatment with a base.

This reaction is carried out in a hydroalcoholic medium at ambient temperature in the presence of at least 1 equivalent of a base such as ammonia, alkaline metal hydroxides or even a tertiary amine such as triethylamine or triethanolamine in accordance with the following reaction:

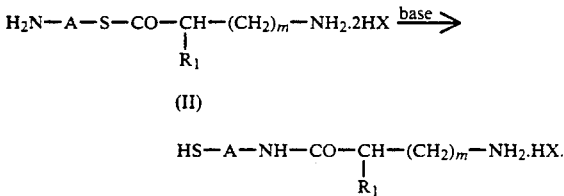

The compounds in accordance with the present invention can also be prepared in a more classic manner by condensation of an N-amino acid protected with an S-acylaminothiol in the presence of an activation agent of peptidic synthesis such as, for example, dicyclohexylcarbodiimide.

The thiol and amine functions are then deprotected by acid or base hydrolysis, such as described, for example, by M. Fatome et al, Eur. J. Med. Chem., 23, (1988), 257-266 or again by J. Oiry et al, J. Med. Chem., 29 (11), 2217-25, (1986).

In the compositions according to the present invention, the reducing agent of general formula (I) is generally present in an amount ranging from 2 to 30% and preferably from 5 to 25% by weight relative to the total weight of the reducing composition.

The pH of the composition is preferably between 4.5 and 11 and more particularly between 6 and 10 and is obtained using an alkaline agent such as, for example, ammonia, monoethanolamine, diethanolamine, triethanolamine, an alkaline or ammonia carbonate or bicarbonate, an alkaline hydroxide or by using an acidifying agent such as, for example, hydrochloric acid, acetic acid, lactic acid, oxalic acid or boric acid.

The reducing composition can also contain other known reducing agents such as, for example, thioglycolic acid, glycerol or glycol monothioglycolate, cysteamine and its $C_1$-$C_4$ acylated derivatives such as N-acetyl cysteamine or N-propionyl cysteamine, cysteine, N-acetylcysteine, N-mercaptoalkylamides of sugars such as N-(2-mercaptoethyl) gluconamide, β-mercaptopropionic acid and its derivatives, thiolactic acid, pantethein or again thioglycerol, sulfites, bisulfites of an alkali or alkaline earth metal and the thiols described in EP patent applications 354.835 and 368.763.

The reducing composition of the present invention can also contain various components such as, for example, cationic polymers such as those employed in the compositions of French patents Nos. 79.32078 and 80.76471 or even cationic polymers of the ionene type such as those used in the compositions of French patent No. 82. 17364, softening agents and principally quaternary ammonium derivatives of lanolin, protein hydrolyzates, waxes, opacifiers, perfumes, dyes, nonionic or cationic surfactants, alcohols such as ethanol, propanol, isopropanol, 1,2-propanediol, 1,2-butanediol or glycerol, treating agents or again penetrating agents such as urea, pyrrolidone or thiamorpholinone.

The reducing composition according to the present invention can also be of the exothermic type, that is to say causing a certain heating during application to the hair, which is agreeable to the person being submitted to the first stage of a permanent waving or uncurling operation.

The vehicle for the compositions in accordance with the present invention is preferably water or a hydroalcoholic solution of a lower alcohol such as ethanol, isopropanol or butanol.

When the composition are intended for a hair uncurling or straightening operation, the reducing composition is preferably in the form of a cream so as to maintain the hair as rigid or stiff as possible. These creams are produced in the form of a "heavy" emulsion, and are based for example on glyceryl stearate, glycol stearate, self-emulsifiable waxes, fatty alcohols and the like. There can also be employed liquids or gels containing thickening agents such as carboxyvinyl polymers or copolymers which "glue" the hair and maintain it in the smoothed position during contact times therewith.

In accordance with a particular embodiment of the present invention, the reducing compounds of general formula (I) can be formed in situ at the time of use starting with their thioester precursors having the following general formula (II):

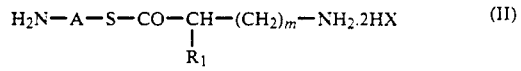

wherein
A, $R_1$ and m have the same meanings as those above for general formula (I), and,
X is Cl or Br.

In effect it has been noted that in the presence of a base such as ammonia, monoethanolamine, diethanolamine, triethanolamine, soda or potash, these thioester precursors are transformed almost instantaneously and quantitatively into the corresponding thiols of general formula (I).

In accordance with this embodiment of the present invention, the thioester precursor, in the solid state, preferably in the form of a powder, is mixed at the time of use with a basic aqueous solution having a pH between 8 and 10, optionally containing various components such as those mentioned above.

The pH of the composition is then adjusted, if necessary, using an alkaline or acidifying agent such as those mentioned previously.

Representative thioesters include principally the following compounds:
2-aminoethyl 3-amino-thiopropionate dihydrochloride,
2-aminoethyl thioglycinate dihydrochloride,
2-aminoethyl thioalaninate dihydrochloride
2-aminoethyl 2-amino thiobutyrate dihydrochloride,
2-aminoethyl thiovalinate dihydrochloride,
2-aminoethyl thioleucinate dihydrochloride,
2-aminoethyl 3-phenyl thioalaninate dihydrochloride,
2-aminoethyl thiomethioninate dihydrochloride,
3-aminopropyl thioglycinate dihydrochloride,
5-aminopentyl thioglycinate dihydrochloride, 2'-(2-aminoethoxy) ethyl thioglycinate dihydrochloride,
3-aminiopropyl 3-aminothiopropionate dihydrochloride,
5-aminopentyl 3-amino thiopropionate dihydrochloride,
2'-(2-aminoethoxy) ethyl 3-amino thiopropionate dihydrochloride,
2-aminoethyl 4-amino thiobutyrate dihydrochloride,
3-aminopropyl 4-amino thiobutyrate dihydrochloride,
5-aminopentyl 4-amino thiobutyrate dihydrochloride,
2'-(2-aminoethoxy) 4-amino thiobutyrate dihydrochloride,
2-aminoethyl 6-amino thiocaproate dihydrochloride,
3-aminopropyl thioalaninate dihydrochloride,
5-aminopentyl thioalaninate dihydrochloride and
2'-(2-aminoethoxy) ethyl thioalaninate dihydrochloride.

The compositions according to the present invention can also be in a form called "self-neutralizing" or again "self-regulating" and in this case, the compound of general formula (I) is combined with at least one disulfide either known for its use in a reducing composition for a self-neutralizing permanent operation or derived from a compound of general formula (I) or from one of its salts and corresponding to the following general formula (III):

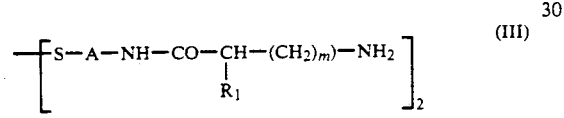

wherein
A, $R_1$ and m have the same meanings as those above for general formula (I).

This disulfide can also be provided in the form of a cosmetically acceptable salt.

Among the known disulfides, there can be mentioned, principally, dithioglycolic acid, dithioglycerol, cystamine, N,N'-diacetylcystamine, cystine, pantetheine and the disulfides described in European patents EP 354.835 and EP 368.763.

Among the disulfides derived from a compound of general formula (I) and corresponding to general formula (III) there can be mentioned:
N,N'(2,1-dithiodiethanediyl) bis [3-amino propionamide],
N,N'-(2,1-dithiodiethanediyl) bis [2-amino acetamide],
N,N'-(2,1-dithiodiethanediyl) bis [2-amino propionamide],
N,N'-[dithiobis (trimethylene)] bis [2-amino propionamide],
N,N'-(2,1-dithiodiethanediyl) bis [α-amino benzene propionamide],
N,N'-(2,1-dithiodiethanediyl) bis [2-amino-4-methyl pentanamide],
N,N'-(2,1-dithiodiethanediyl) bis [4-amino butanamide],
N,N'-[dithiobis(trimethylene)] bis [3-amino propionamide],
5,5'-[dithiobis (2,1-ethanediylimino)] bis [4-amino-5-oxo pentanoic] acid,
N,N'-[dithiobis (trimethylene)] bis [2-amino acetamide],
N,N'-[dithiobis (pentamethylene)] bis [2-amino acetamide],
N,N'-[dithiobis (pentamethylene)] bis [4-amino butanamide],
N,N'-[dithiobis (2-ethyloxyethyl)] bis [2-amino acetamide] and
N,N'-(2,1-dithiodiethanediyl) bis [6-amino hexanamide].

In the self-neutralizing compositions the disulfide is generally present in a molar ratio of 0.5 to 2.5 and preferably from 1 to 2 relative to the compound of general formula (I) or of its salts (see U.S. Pat. No. 3,768,490).

The disulfides of general formula (III) are obtained by oxidation of the compounds of general formula (I) either in air or by using known oxidizing agents as, for example, $H_2O_2$ in the presence optionally of metallic salts such as, for example, ferrous salts.

The present invention also relates to, as new industrial products, amino-mercaptoalkylamides having the following general formula (IV):

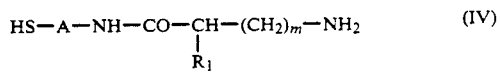

wherein
A, $R_1$ and n have the same meanings as given above for general formula (I) with the exception of compounds in which:
(i) A represents —$(CH_2)_2$— and m is 0 or 1, and $R_1$ represents hydrogen, linear or branched alkyl having 1-5 carbon atoms, benzyl or 2-carboxyethyl, and
(ii) A represents —$(CH_2)_3$— and m is 1, and $R_1$ represents hydrogen,
and the salts of said compound of formula (IV).

The compounds of formula (IV) are prepared in accordance with the methods mentioned for the preparation of the compounds of formula (I).

Represenstative amino-mercaptoalkylamides of general formula (IV) include principally:
2-amino N-(3-mercaptopropyl) acetamide,
2-amino N-(5-mercaptopentyl) acetamide,
2-amino N-[2'(2-mercaptoethoxy) ethyl] acetamide,
2-amino N-(3-mercaptopropyl) propionamide,
2-amino N-(5-mercaptopentyl) propionamide,
2-amino N-(2-mercapto-2-ethoxyethyl) propionamide,
3-amino N-(3-mercaptopropyl) propionamide,
3-amino N-(5-mercaptopentyl) propionamide,
3-amino N-[2'-(2-mercaptoethoxy) ethyl] propionamide,
4-amino N-(2-mercaptoethyl) butanamide,
4-amino N-(3-mercaptopropyl) butanamide,
6-amino N-(5-mercaptopentyl) butanamide,
4-amino N-[2'-(2-mercaptoethoxy) ethyl] butanamide and
6-amino N-(2-mercaptoethyl) hexanamide, as well as their hydrochlorides.

The present invention also relates to new disulfides having the following general formula (V):

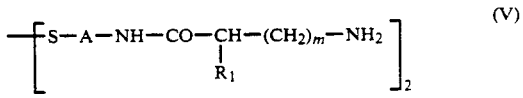

wherein

A, $R_1$ and m have the same meanings as those given above for general formula (IV).

Among the disulfides of formula (V) there can be mentioned principally:

N,N'-[dithiobis (trimethylene)] bis [2-amino acetamide],

N,N'-[dithiobis (pentamethylene)] bis [2-amino acetamide],

N,N'-[dithiobis (2-ethyloxyethyl)] bis [2-amino acetamide],

N,N'-[2,1-dithiodiethanediyl] bis [6-aminohexanamide],

N,N'-[2,1-dithiodiethanediyl] bis [4-amino butanamide],

N,N'-[dithiobis (trimethylene)] bis [4-amino butanamide],

N,N'-[dithiobis (pentamethylene)] bis [4-amino butanamide],

N,N'-[dithiobis (trimethylene)] bis [2-amino propionamide],

N,N'-[dithiobis (trimethylene)] bis [3-amino propionamide],]

N,N'-[dithiobis (pentamethylene)] bis [3-amino propionamide] and

N,N'-[dithiobis (2-ethyloxyethyl)] bis [3-amino propionamide].

The present invention also relates to, as new products, thioesters having the following general formula (VI):

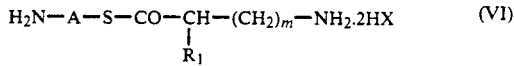

wherein

A, X, $R_1$ and m have the same meanings as those given above for general formula (II), with the exception of compounds wherein:

(i) A represents $-(CH_2)_2-$, m is 0 or 1 and $R_1$ represents hydrogen, and (ii) A represents $-(CH_2)_2-$, m is 0 and $R_1$ represents methyl, ethyl, isopropyl, isobutyl, methylthioethyl or benzyl.

The compounds of general formula (VI) are obtained by the reaction of an aminothiol (1) with an acid halide of an amino acid (2) at a temperature between 40° and 110° C. in the presence or not of an inert organic solvent such as, for example, dichloromethane, 1,2-dichloroethane, chloroform, carbon tetrachloride, acetonitrile, toluene, dioxan, tetrahydrofuran, 1,2-dimethoxyethane, N-methylpyrrolidone, dimethylacetamide or dimethylformamide, or a mixture of these solvents in accordance with the following reaction:

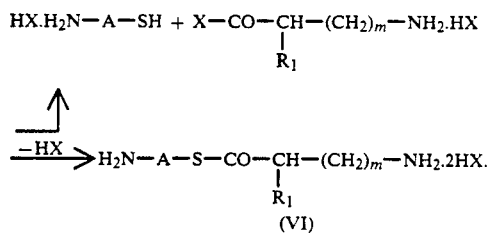

The aminothiols and the acid halides employed are prepared in accordance with classic methods for the synthesis of these compounds.

Representative thioesters of general formula (VI) include principally:

3-aminopropyl thioglycinate dihydrochloride, 5-aminopentyl thioglycinate dihydrochloride, 2-amino-2'-ethoxyethyl thioglycinate dihydrochloride, 2-aminoethyl 4-amino thiobutyrate dihydrochloride, 3-aminopropyl 4-amino thiobutyrate dihydrochloride, 5-aminopentyl 4-amino thiobutyrate dihydrochloride, 2'-(2-aminoethoxy) ethyl 4-amino thiobutyrate dihydrochloride, 2-aminoethyl 6-amino thiocaproate dihydrochloride, 3-aminopropyl thioalaninate dihydrochloride, 5-aminopentyl thioalaninate dihydrochloride and 2'-(2-aminoethoxy) ethyl thioalaninate dihydrochloride.

The present invention also relates to a process for the permanent deformation of hair comprising, in a first stage, reducing the disulfide bonds of keratin by applying, for a period of about 5 to 60 minutes, a reducing composition such as defined above and then in a second stage, reforming the said bonds by applying to the hair an oxidizing composition or optionally by permitting the oxygen of the air to act on the hair.

The present invention also relates to a process for waving the hair in which a reducing composition such as defined above is applied on moistened hair previously rolled up on rollers having a diameter of 4 to 20 mm, the composition optionally being able to be applied in proportion of the rolling of the hair. The reducing composition is permitted to act on the hair for a period of time ranging from 5 to 60 minutes, preferably 5 to 30 minutes. The hair is then thoroughly rinsed after which there is applied, on the rolled up hair, an oxidizing composition so as to reform the disulfide bonds of the keratin. The oxidizing composition remains in contact with the hair for a period of time of 2 to 10 minutes. After having removed the rollers, the hair is thoroughly rinsed.

The oxidation composition or the oxidizing agent is of the type currently employed and contains as the oxidizing agent, $H_2O_2$, an alkaline bromate, a polythionate or a mixture of an alkaline bromate and a persalt. The $H_2O_2$ concentration can vary from 1 to 20 volumes and preferably from 1 to 10 volumes; the concentration of the alkaline bromate from 2 to 12 percent and that of the persalt from 0.1 to 15 percent by weight relative to the total weight of the oxidizing composition. The pH of the oxidizing composition is generally between 2 and 10. The oxidation can be carried out immediately or can be delayed.

The present invention also relates to a process for uncurling or straightening the hair in which there is applied on the hair a reducing composition in accordance with the invention. The hair is then submitted to a mechanical deformation so as to fix the hair in a new form by smoothing the hair with a comb having large teeth, with the back of a comb or with the hand. After a contact time of 5 to 60 minutes, in particular 5 to 30 minutes, the hair is again smoothed and is then carefully rinsed. An oxidizing or fixing composition such as defined above, is then applied to the hair and is permitted to remain in contact therewith for about 2 to 10 minutes. The hair is then thoroughly rinsed.

There is now given as an illustration and without any limiting character several examples of the preparation of the compounds according to the invention as well as examples of reducing compositions according to the invention and their use in a process for the permanent deformation of hair.

EXAMPLES OF PREPARATION

Example 1—Preparation of 2-amino N-(2-mercaptoethyl) propionamide hydrochloride (a) 2-aminoethyl thioalaninate dihydrochloride To a suspension of 11.4 g (0.1 mole) of cysteamine hydrochloride in 350 cm$^3$ of anhydrous acetonitrile, there are added, under an inert atmosphere, 14.4 g of DL-alanine acid chloride hydrochloride which mixture is then heated to 80° C. with stirring. After two hours, the reaction is completed (end of the evolution of HCl). The reaction mixture is cooled to ambient temperature and the thioester formed is dried and recrystallized in methanol. After drying under a vacuum at 50° C., 13.8 g of the dihydrochloride of 2-aminoethyl thioalaninate in the form of a white solid having a melting point of 226° C. are obtained.

The NMR$^1$H 80 MHz spectrum conforms to the expected structure.

Elemental analysis: $C_5H_{12}N_2OS.2HCl$

|            | C %   | H %  | N %   | O %  | S %   | Cl %  |
|------------|-------|------|-------|------|-------|-------|
| Calculated | 27.16 | 6.38 | 12.67 | 7.23 | 14.50 | 32.06 |
| Found      | 27.25 | 6.36 | 12.60 | 7.45 | 14.40 | 32.02 |

(b) To a suspension of 22.1 g of the 2-aminoethyl thioalaninate dihydrochloride (0.1 mole), obtained above, in 50 cm$^3$ of isopropanol, thre are slowly added, under an inert atmosphere, 20.4 cm$^3$ (0.15 mole) of a 2.5% aqueous ammonia solution. The resulting solution is evaporated to dryness under reduced pressure. The residue is taken up in 100 cm$^3$ of ethanol. The insoluble ammonium chloride is separated by filtration on fritted glass. The filtrate is evaporated to dryness and dried under a vacuum at 50° C. 17.5 g of 2-amino N-(2-mercaptoethyl) propionamide in the form of a white solid whose melting point is 141° C. are obtained.

The NMR$^1$H 80 MHz spectrum conforms to the expected structure.

Elemental analysis: $C_5H_{12}N_2OS.HCl$

|            | C %   | H %  | N %   | O %   | S %   | Cl %  |
|------------|-------|------|-------|-------|-------|-------|
| Calculated | 32.52 | 7.09 | 15.17 | 8.66  | 17.36 | 19.7  |
| Found      | 31.63 | 7.17 | 14.80 | 10.29 | 16.97 | 18.69 |

Example 2—Preparation of 2-amino N-(2-mercaptoethyl) acetamide hydrochloride (a) 2-aminoethyl thioglycinate dihydrochloride To a suspension of 11.4 g (0.1 mole) of cystamine hydrochloride in 50 cm$^3$ of anhydrous acetonitrile, there are added under an inert atmosphere and with stirring, 13 g (0.1 mole) of glycine acid chloride hydrochloride. The mixture is then heated for 3 hours at 75° C. After cooling to ambient temperature, the crude thioester is dried and then purified by two successive washings in 40 cm$^3$ of methanol. After drying under a vacuum at 50° C., 15.1 g of 2-aminoethyl thioglycinate dihydrochloride in the form of a white solid which decomposes at 165° C. are obtained. The NMR$^1$H 80 MHz spectrum conforms to the expected structure.

Elemental analysis: $C_4H_{10}N_2OS.2HCl$

|            | C %   | H %  | N %   | O %  | S %   | Cl %  |
|------------|-------|------|-------|------|-------|-------|
| Calculated | 23.20 | 5.84 | 13.53 | 7.72 | 15.48 | 34.23 |
| Found      | 23.37 | 5.93 | 13.32 | 7.96 | 15.42 | 33.99 |

(b) To a suspension of 30 g (0.145 mole) of 2-aminoethyl thioglycinate dihydrochloride, obtained above, there are slowly added over a 15 minute period, at ambient temperature under an inert atmosphere and with stirring, 152 cm$^3$ of a 5% aqueous ammonia solution. The resulting solution is evaporated to dryness under reduced pressure. 100 cm3 of isopropanol are added to the residue which is again evaporated to dryness. 200 cm$^3$ of ethanol are added and the mixture is stirred at ambient temperature to finely disperse it. The ammonium chloride is filtered off on fritted glass. The filtrate is evaporated to dryness. The resulting white solid (23.3 g) is recrystallized in isopropanol. After draining and drying under a vacuum 16.4 g of 2-amino N-(2-mercaptoethyl) acetamide hydrochloride in the form of a white solid having a melting point of 122° C. are obtained.

The NMR$^1$H 250 MHz and 13C spectra conform to the expected structure.

Elemental analysis: $C_4H_{10}N_2OS.HCl$

|            | C %   | H %  | N %   | O %   | S %   | Cl %  |
|------------|-------|------|-------|-------|-------|-------|
| Calculated | 28.15 | 6.50 | 16.41 | 9.37  | 18.79 | 20.77 |
| Found      | 27.74 | 6.57 | 16.26 | 10.33 | 18.41 | 20.46 |

Example 3- Preparation of 2-aminoethyl 4-amino thiobutyrate dihydrochloride

To a suspension of 11.4 g (0.1 mole) of cysteamine hydrochloride in 40 cm3 of anhydrous acetonitrile, there are added, under an inert atmosphere and with stirring, 15.8 g (0.1 mole) of 4-amino butyric acid chloride hydrochloride. The mixture is heated for 5 hours at 80° C. After cooling to ambient temperature, the white solid is drained on fritted glass and then recrystallized in a 50/50 ethanol/methanol mixture. After drying under a vacuum at 50° C., 17.6 of 2-amino ethyl 4-amino thiobutyrate dihydrochloride in the form of a white solid whose melting point is 186° C. are obtained.

The NMR$^1$H 80 MHz spectrum conforms to the expected structure.

Elemental analysis: $C_6H_{14}N_2OS.2HCl$

|            | C %   | H %  | N %   | O %  | S %   | Cl %  |
|------------|-------|------|-------|------|-------|-------|
| Calculated | 30.64 | 6.86 | 11.91 | 6.80 | 13.63 | 30.15 |
| Found      | 29.88 | 6.92 | 11.59 | 7.40 | 13.40 | 29.33 |

Example 4- Preparation of 2-aminoethyl 6-amino thiocaproate dihydrochloride

This compound is prepared in accordance with the same procedures as in Example 3 but starting with 18.6 g (0.1 mole) of 6-aminocaproic acid chloride hydrochloride. After heating for 4 hours at 80° C., the reaction mixture is cooled, dryed and recrystallized in a 70/30 ethanol/methanol mixture. After drying under a vacuum at 50° C., 15.8 g of 2-aminoethyl 6-amino thiocaproate dihydrochloride in the form of a white solid having a melting point of 181° C. are obtained.

The NMR$^1$H 80 MHz spectrum conforms to the expected structure.

Elemental analysis: $C_8H_{18}N_2OS.2HCl$.

|  | C % | H % | N % | O % | S % | Cl % |
|---|---|---|---|---|---|---|
| Calculated | 36.50 | 7.66 | 10.64 | 6.08 | 12.18 | 26.94 |
| Found | 36.48 | 7.22 | 11.38 | 6.44 | 12.70 | 26.72 |

Example 5—Preparation of N,N'-(2,1-dithiodiethanediyl) bis [2-amino acetamide]

To a solution of 50.5 g (0.29 mole) of 2-amino N-(2-mercaptoethyl) acetamide hydrochloride, obtained in Example 2, in 500 cm$^3$ of absolute ethanol, there are slowly added 15.2 cm$^3$ (0.15 mole) of $H_2O_2$ at 110 volumes while maintaining the temperature lower than 25° C. After 24 hours of stirring, the crystallization of the disulfide is complete. The mixture is drained on fritted glass, washed with 100 cm$^3$ of absolute ethanol and dried under a vacuum at 60° C. 43.1 g of white crystals of N,N'-(2,1-dithiodiethanediyl) bis [2-amino acetamide] having a melting point of 168°–170° C. are obtained.

The NMR$^1$H 80 MHz spectrum conforms to the expected structure.

Elemental analysis: $C_8H_{18}N_4O_2S_2.2HCl$

|  | C % | H % | N % | O % | S % | Cl % |
|---|---|---|---|---|---|---|
| Calculated | 28.32 | 5.94 | 16.51 | 9.43 | 18.90 | 20.90 |
| Found | 28.04 | 6.09 | 16.23 | 10.45 | 18.69 | 20.64 |

Example 6—Preparation of 3-aminopropyl 4-amino thiobutyrate dihydrochloride

A suspension of 12.8 g (0.1 mole) of 3-mercapto propylamine hydrochloride and 11.58 g (0.1 mole) of 4-amino butyric acid chloride hydrochloride in 75 cm$^3$ of anhydrous acetonitrile is stirred under an inert atmosphere and heated for 4 hours at reflux.

After cooling to ambient temperature, the crude thioester is drained, washed with iced methanol and then recrystallized in a 75/25 ethanol/methanol mixture.

After drying under a vacuum at 50° C., 17.5 g of 3-aminopropyl 4-amino thiobutyrate dihydrochloride in the form of a white solid whose melting point is 205° C. are obtained.

The NMR$^1$H 80 MHz spectrum conforms to the expected structure.

Example 7- Preparation of 2-(2-aminoethoxy) ethyl thioglycinate dihydrochloride

A suspension of 15.7 g (0.1 mole) of 2'-(2-mercapto ethoxy) ethylamine hydrochloride and 13 g (0.1 mole) of glycine acid chloride hydrochloride in 120 cm$^3$ of anhydrous acetonitrile, is heated under an inert atmosphere with stirring at 30° C. for 30 minutes, and then at reflux for 1 hour 30 minutes.

After cooling to ambient temperature, the crude thioester is drained and then recrystallized in about 250 cm$^3$ of ethanol.

After drying under a vacuum at 40° C., 10 g of 2'-(2-aminoethoxy) ethyl thioglycinate dihydrochloride in the form of a white solid having a melting point (decomposition) of 145° C. are obtained.

The NMR$^1$H 80 MHz spectrum conforms to the expected structure.

Example 8—Preparation of 5-aminopentyl thioglycinate dihydrochloride

A suspension of 15.55 g (0.1 mole) of 5-mercapto pentylamine hydrochloride and 13 g (0.1 mole) of glycine acid chloride hydrochloride in 60 cm$^3$ of anhydrous acetonitrile, is heated under an inert atmosphere with stirring for 3 hours at reflux.

After cooling to ambient temperature, the crude thioester is drained, washed with isopropanol and then recrystallized in an ethanol/methanol mixture.

After drying under a vacuum at 30° C., 18.6 g of 5-aminopentyl thioglycinate dihydrochloride in the form of a white solid having a melting point (decomposition) of 230° C. are obtained.

The NMR$^1$H spectrum conforms to the expected structure.

EXAMPLES OF COMPOSITIONS

Example A

In accordance with the present invention a reducing composition for the permanent deformation of hair is prepared by admixing the following components:

| A. Reducing Composition | |
|---|---|
| 2-amino N-(2-mercaptoethyl) acetamide hydrochloride | 17 g |
| Monoethanolamine, sufficient amount for pH = 8.5 | |
| Oleocetyl dimethyl hydroxyethyl ammonium chloride | 0.3 g |
| Preservative | 0.2 g |
| Perfume | 0.8 g |
| Demineralized water, sufficient amount for | 100 g |

This composition is applied to moistened hair previously rolled up on rollers. After permitting it to remain in contact with the hair for 15 minutes, the hair is thoroughly rinsed with water. The following oxidizing composition is then applied to the hair:

| B. Oxidizing Composition | |
|---|---|
| $H_2O_2$ | 1.5 g |
| Sodium lauryl ether sulfate, oxyethylenated with 2 moles of ethylene oxide | 3.75 g |
| Citric acid | 0.5 g |
| Sodium hydrogenphosphate | 0.5 g |
| Perfume | 0.3 g |
| Demineralized water, sufficient amount for | 100 g |

The oxidizing composition is permitted to act for about 5 minutes. The rollers are then removed and the hair is thoroughly rinsed with water. After drying under a hood, the hair exhibits beautiful curls.

In accordance with the same embodiments in Example A, a permanent deformation of hair is carried out using the reducing and oxidizing compositions of the following Examples B to P:

Example B

| A. Reducing Composition | |
|---|---|
| 2-amino N-(2-mercaptoethyl) acetamide hydrochloride | 21 g |
| Ethylenediamine tetraacetic acid | 0.2 g |
| Triethanolamine, sufficient for pH = 6.8 | |
| Lauramine oxide, sold under the trade name "Aromox DMMCD/W" by Akzo | 2.15 g |
| Perfume | 0.6 g |
| B. Oxidizing Composition | |
| $H_2O_2$ | 2.0 g |
| Oleocetyl dimethyl hydroxyethyl ammonium chloride | 0.3 g |
| Phosphoric acid | 0.5 g |
| p-ethoxyacetonilide (phenacetin) | 0.1 g |
| Protein hydrolyzate | 0.5 g |
| Perfume | 0.5 g |
| Demineralized water, sufficient amount for | 100 g |

Example C

| A. Reducing Composition | |
|---|---|
| 2-aminoethyl thioglycinate dihydrochloride | 10 g |
| Ammoniacal solution, 20% $NH_3$ | 4.1 g |
| Monoethanolamine, sufficient amount for pH = 8.0 | |
| Ammonium hydrogencarbonate | 2.0 g |
| Cocoamidopropylbetaine, sold under the trade name "Tegobetaine HS" by Goldschmidt | 0.9 g |
| Demineralized water, sufficient amount for | 100 g |
| B. Oxidizing Composition | |
| $H_2O_2$ | 2.5 g |
| Sodium stannate | 0.03 g |
| N,N-dimethyl N-2 propenyl-2-propene-1 ammonium chloride (poly quaternium-6) sold under the trade name "Merquat 100" by Merck | 1.25 g |
| Citric acid | 0.6 g |
| Perfume | 0.5 g |
| Demineralized water, sufficient amount for | 100 g |

Example D

| A. Reducing Composition | |
|---|---|
| 2-aminoethyl thioglycinate dihydrochloride | 15 g |
| N,N'-(2,1-dithioethanediyl) bis [2-amino acetamide] | 4.5 g |
| Pentasodium salt of diethylene triamine pentacetic acid | 0.2 g |
| Monoethanolamine, sufficient amount for pH = 8.9 | |
| Hydrogenated castor oil oxyethylenated with 60 moles of ethylene oxide, sold under the trade name "NIKKOL HCO 60" by Nikko Chemical | 4 g |
| N,N-dimethyl N-2 propenyl-2-propene 1-ammonium chloride (polyquaternium 7) sold under the trade name "Merquat 550" by Merck | 3.8 g |
| Perfume | 0.3 g |
| Demineralized water, sufficient amount for | 100 g |
| B. Oxidizing Composition | |
| $H_2O_2$ (200 volumes) | 4.8 g |
| Stabilizer | 0.1 g |
| D. Panthenol | 1.0 g |
| 4'-α-dimethyl-α-(4-methyl-3-pentenyl)-3-cyclohexene methanol (Bisabolol), sold under the trade name "Dragosantol 2/012681" by Dragoco | 0.3 g |
| Lauryl dimethyl amine oxide | 0.7 g |
| Perfume | 0.4 g |
| Lactic acid, sufficient amount for pH = 3.0 | |
| Demineralized water, sufficient amount for | 100 g |

Example E

| A. Reducing Composition | |
|---|---|
| 2-aminoethyl thioglycinate dihydrochloride | 5 g |
| 2-aminoethyl 4-amino thiobutyrate dihydrochloride | 6.5 g |
| Ammoniacal solution, 20% | 4.4 g |
| Monoethanolamine, sufficient amount for pH = 7.5 | |
| Oleyl ether oxyethylenated with 20 moles of ethylene oxide | 6.0 g |
| Lauryl ether oxyethylenated with 23 moles of ethylene oxide | 1.0 g |
| Pentasodium salt of diethylene triamine pentacetic acid | 0.5 g |
| Perfume | 0.3 g |
| Demineralized water, sufficient amount for | 100 g |
| B. Oxidizing Composition | |
| $H_2O_2$ | |
| Sodium lauryl ether sulfate oxyethylenated with 2 moles of ethylene oxide | 3.75 g |
| Citric acid | 0.5 g |
| Sodium hydrogenphosphate | 0.5 g |
| Perfume | 0.3 g |
| Demineralized water, sufficient amount for | 100 g |

Example F

| A. Reducing Composition | |
|---|---|
| 2-aminoethyl thioglycinate dihydrochloride | 4 g |
| 2-aminoethyl thioalaninate dihydrochloride | 3 g |
| 2-amino N-(2-mercaptoethyl) propionamide hydrochloride | 2.5 g |
| Monoethanolamine, sufficient amount for pH = 8.7 | |
| Cetrimonium chloride, sold under the trade name "Dehyquart A" by Henkel | 1 g |
| Perfume | 0.7 g |
| Demineralized water, sufficient amount for | 100 g |
| B. Oxidizing Composition | |
| Sodium bromate | 8.0 g |
| Triethanolamine, sufficient amount for pH = 8.0 | |
| Hydrated monosodium phosphate ($12H_2O$) | 0.3 g |
| Hydrated trisodium phosphate ($2H_2O$) | 0.5 g |
| Cocoamidopropylbetaine, sold under the trade name "Tegobetaine HS" by Goldschmidt | 1.0 g |
| Perfume | 0.4 g |
| Demineralized water, sufficient amount for | 100 g |

Example G

| A. Reducing Composition | |
|---|---|
| 2-aminoethyl thioglycinate dihydrochloride | 3.0 g |
| L-cysteine | 5.0 g |
| Monoethanolamine, sufficient amount for pH = 9.3 | |
| Stearic ester polyoxyethylenated with 8 moles of ethylene oxide, sold under the trade name "Myrj 45" by ICI | 1 g |
| Preservative | 0.4 g |
| Perfume | 0.3 g |
| Demineralized water, sufficient amount for | 100 g |
| B. Oxidizing Composition | |
| $H_2O_2$ | 2.5 g |
| Sodium stannate | 0.02 g |
| Ammonium lauryl sulfate | 1.5 g |
| Protein hydrolyzate | 0.6 g |
| Citric acid | 0.5 g |

-continued

| | |
|---|---|
| Perfume | 0.4 g |
| Demineralized water, sufficient amount for | 100 g |

Example H

| | |
|---|---|
| A. Reducing Composition | |
| 2-aminoethyl thioglycinate dihydrochloride | 2.0 g |
| N-acetylcysteamine | 6.0 g |
| Ammoniacal solution, sufficient amount for pH = 8.0 | |
| Ammonium hydrogen carbonate | 2.0 g |
| N,N-dimethyl N-2 propenyl-2-propene-1 ammonium chloride (polyquaternium-6) sold under the trade name "Merquat 100" by Merck | 2.5 g |
| Collagen hydrolyzate | 0.5 g |
| Oleocetyl dimethyl hydroxyethyl ammonium chloride | 1.0 g |
| Perfume | 0.8 g |
| Demineralized water, sufficient amount for | 100 g |
| B. Oxidizing Composition | |
| $H_2O_2$ (200 volumes) | 4.8 g |
| Stabilizer | 0.1 g |
| D. Panthenol | 1.0 g |
| 4'-α-dimethyl-α-(4-methyl-3-pentenyl)-3-cyclohexene methanol (Bisabolol), sold under the trade name "Dragosantol 2/012681" by Dragoco | 0.3 g |
| Lauryl dimethyl amine oxide | 0.7 g |
| Perfume | 0.4 g |
| Lactic acid, sufficient amount for pH = 3.0 | |
| Demineralized water, sufficient amount for | 100 g |

Example I

| | |
|---|---|
| A. Reducing Composition | |
| 2-aminoethyl thioglycinate dihydrochloride | 5.5 g |
| 2-aminoethyl 6-amino thiocaproate dihydrochloride | 7.3 g |
| Ammoniacal solution (20%) Monoethanolamine, sufficient amount for pH = 8.3 | 5.1 g |
| Cocoamidopropylbetaine, sold under the trade name "Tegobetaine HS" by Goldschmidt | 0.9 g |
| Vinyl pyrrolidone/methacrylamidopropyl trimethyl ammonium chloride copolymer 20% in water, sold under the trade name "Gafquat HS" by GAF | 1.0 g |
| Preservative | 0.2 g |
| Perfume | 0.7 g |
| Demineralized water, sufficient amount for | 100 g |
| B. Oxidizing Composition | |
| $H_2O_2$ | 2.0 g |
| Oleocetyl dimethyl hydroxyethyl ammonium chloride | 0.3 g |
| Phosphoric acid | 0.5 g |
| p-ethoxyacetonilide (Phenacetin) | 0.1 g |
| Protein hydrolyzate | 0.8 g |
| Perfume | 0.5 g |
| Demineralized water, sufficient amount for | 100 g |

Example J

| | |
|---|---|
| A. Reducing Composition | |
| 2-aminoethyl thioglycinate dihydrochloride | 1.5 g |
| Cysteamine, HCl | 5.2 g |
| Monoethanolamine, sufficient amount for pH = 9.5 | |
| Cetyl trimethyl ammonium chloride | 1.0 g |
| Perfume | 0.6 g |
| Preservative | 0.15 g |
| Demineralized water, sufficient amount for | 100 g |
| B. Oxidizing Composition | |
| Sodium bromate | 8 g |
| Triethanolamine, sufficient amount for pH = 8.0 | |
| Hydrated monosodium phosphate (12H$_2$O) | 0.3 g |
| Hydrated trisodium phosphate (2H$_2$O) | 0.5 g |
| Cocoamidopropylbetaine, sold under the trade name "Tegobetaine HS" by Goldschmidt | 1.0 g |
| Perfume | 0.4 g |
| Demineralized water, sufficient amount for | 100 g |

Example K

| | |
|---|---|
| A. Reducing Composition | |
| 2-aminoethyl thioglycinate dihydrochloride | 5.5 g |
| 2-aminoethyl 3-amino thiopropionate dihydrochloride | 7.3 g |
| Ammonia (20%) Monoethanolamine, sufficient amount for pH = 8.3 | 5.1 g |
| Cocoamidopropylbetaine, sold under the trade name "Tegobetaine HS" by Goldschmidt | 0.9 g |
| Vinyl pyrrolidone/methacrylamidopropyl trimethyl ammonium chloride copolymer, 20% in water, sold under the trade name "Gafquat HS 100" by GAF | 1.0 g |
| Preservative | 0.2 g |
| Perfume | 0.7 g |
| Demineralized water, sufficient amount for | 100 g |
| B. Oxidizing Composition | |
| $H_2O_2$ | 2.0 g |
| Oleocetyl dimethyl hydroxyethyl ammonium chloride | 0.3 g |
| Phosphoric acid | 0.5 g |
| p-ethoxyacetonilide (Phenacetin) | 0.1 g |
| Protein hydrolyzate | 0.8 g |
| Perfume | 0.5 g |
| Demineralized water, sufficient amount for | 100 g |

Example L

| | |
|---|---|
| A. Reducing Composition | |
| 3-amino N-(2-mercaptoethyl) propionamide (Aletheine) | 18 g |
| Oleocetyl dimethyl hydroxyethyl ammonium chloride | 1.3 g |
| Pentasodium salt of diethylenetriamino pentacetic acid | 0.2 g |
| Ammonia (20%), sufficient amount for pH = 8.5 | |
| Demineralized water, sufficient amount for | 100 g |
| B. Oxidizing Composition | |
| $H_2O_2$ (100 volumes) | 4.8 g |
| 8-hydroxyquinoline sulfate | 0.0125 g |
| p-ethoxyacetomilide (phenacetin) | 0.05 g |
| Oleocetyldimethylhydroxyethyl ammonium chloride | 0.3 g |
| Citric acid, sufficient amount for pH = 3.0 | |
| Demineralized water, sufficient amount for | 100 g |

In this Example the reducing composition can be obtained, at the time of use, starting the thioester precursor of aletheine.

In accordance with this embodiment, 22.1 g of 2-aminoethyl 3-amino thioprionate in powder form are mixed with a basic aqueous solution having the following composition:

Example M

A. Reducing Composition

| | |
|---|---|
| 2-aminoethyl 3-amino thiopropionate dihydrochloride | 18.4 g |
| Ammonia (20% solution) sufficient amount for pH = 6.9 | |
| Vinyl pyrrolidone/dimethylaminoethyl methacrylate copolymer mixture quaternized by dimethyl sulfate, sold under the trade name "Gafquat 755" by GAF | 5.0 g |
| Sodium cocoamido ethyl (N-hydroxyethyl, N-carboxymethyl) glycinate, sold under the trade name "Miranol C2M concentre NP" by Miranol | 1.3 g |
| Perfume | 0.5 g |
| Preservative | 0.2 g |
| Demineralized water, sufficient amount for | 100 g |

B. Oxidizing Composition

| | |
|---|---|
| $H_2O_2$ | 2.5 g |
| Stabilizer | 0.1 g |
| Lauramine oxide, sold under the trade name "Aromex DMMCD/W" by Akzo | 2.15 g |
| Perfume | 0.4 g |
| Lactic acid, sufficient amount for pH = 3.0 | |
| Demineralized water, sufficient amount for | 100 g |

Example N

A. Reducing Composition

| | |
|---|---|
| 2-aminoethyl 3-amino thiopropionate dihydrochloride | 16 g |
| N,N'-(2,1-dithioethanediyl) bis [3-amino propionamide] dihydrochloride | 7.5 g |
| Ammonia (20% solution) sufficient amount for pH = 7.0 | |
| Monoethanolamine | 3.3 g |
| Perfume | 0.7 g |
| Preservative | 0.2 g |
| Oleocetyl dimethyl hydroxyethyl ammonium chloride | 0.3 g |
| Demineralized water, sufficient amount for | 100 g |

B. Oxidizing Composition

| | |
|---|---|
| Sodium bromate | 8.0 g |
| Triethanolamine, sufficient amount for pH = 8.0 | |
| Hydrated monosodium phosphate (12H$_2$O) | 0.3 g |
| Hydrated trisodium phosphate (2H$_2$O) | 0.5 g |
| Cocoamidopropyl betaine, sold under the trade name "Tegobetaine HS" by Goldschmidt | 2.8 g |
| Demineralized water, sufficient amount for | 100 g |

Example O

A. Reducing Composition

| | |
|---|---|
| 2-aminoethyl 3-amino thiopropionate dihydrochloride | 3 g |
| L-cysteine | 5 g |
| Monoethanolamine, sufficient amount for pH = 9.3 | |
| Stearic ester polyoxyethylenated with 8 moles of ethylene oxide, sold | 1 g |
| Oleocetyldimethylhydroxyethyl ammonium chloride | 1.3 g |
| Pentasodium salt of diethylenetriamino pentacetic acid | 0.2 g |
| Ammonia, sufficient amount for pH = 8.5 | |
| Demineralized water, sufficient amount for | 100 g | under the trade name "Myrj 45" by ICI

| | |
|---|---|
| Preservative | 0.4 g |
| Perfume | 0.3 g |
| Demineralized water, sufficient amount for | 100 g |

B. Oxidizing Composition

| | |
|---|---|
| $H_2O_2$ | 2.5 g |
| Sodium stannate | 0.02 g |
| Ammonium lauryl sulfate | 1.5 g |
| Protein hydrolyzate | 0.6 g |
| Citric acid | 0.5 g |
| Perfume | 0.4 g |
| Demineralized water, sufficient amount for | 100 g |

Example P

A. Reducing Composition

| | |
|---|---|
| 2-aminoethyl 3-amino thiopropionate dihydrochloride | 1.5 g |
| Cysteamine, HCl | 5.2 g |
| Monoethanolamine, sufficient amount for pH = 9.5 | |
| Cetyl trimethyl ammonium chloride | 1.0 g |
| Preservative | 0.15 g |
| Perfume | 0.6 g |
| Demineralized water, sufficient amount for | 100 g |

B. Oxidizing Composition

| | |
|---|---|
| Sodium bromate | 8 g |
| Triethanolamine, sufficient amount for pH = 8.0 | |
| Hydrated monosodium phosphate (12H$_2$O) | 0.3 g |
| Hydrated trisodium phosphate (2H$_2$O) | 0.5 g |
| Cocoamidopropyl betaine, sold under the trade name "Tegobetaine HS" by Goldschmidt | 1.0 g |
| Perfume | 0.4 g |
| Demineralized water, sufficient amount for | 100 g |

We claim:

1. A cosmetic composition for the first stage of a permanent deformation of hair operation, said composition comprising, in a cosmetically acceptable vehicle, as a reducing agent, at least one amino mercaptoalkylamide having the formula

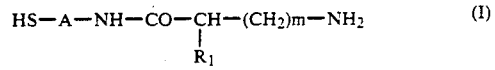

wherein

A represents the divalent radical, —(CH$_2$)$_n$— wherein n is a whole number between 2 and 5, or the divalent radical, —(CH$_2$)$_2$—O—(CH$_2$)$_2$—, m is 0 or a whole number between 1 and 4, (i) when m is 0, R$_1$ represents hydrogen, methyl, ethyl, isopropyl, isobutyl, 2-methyl butyl, benzyl, 4-amino butyl, 3-guanidino propyl, 2-methylthioethyl, carboxymethyl or 2-carboxyethyl, and (ii) when m is a whole number from 1 to 4, R$_1$ represents hydrogen or lower alkyl having 1-5 carbon atoms, and the salts of said compound of formula (I).

2. The composition of claim 1 wherein said salt of said compound of formula (I) is selected from the group consisting of hydrochloride, hydrobromide, citrate and oxalate.

3. The composition of claim 1 wherein said compound of formula (I) is selected from the group consisting of 3-amino N-(2-mercaptoethyl) propionamide or aletheine,
2-amino N-(2-mercaptoethyl) acetamide,
2-amino N-(3-mercaptopropyl) acetamide,
2-amino N-(5-mercaptopentyl) acetamide,
2-amino N-[2'(2-mercaptoethoxy) ethyl] acetamide,
2-amino N-(2-mercaptoethyl) propionamide,
2-amino N-(3-mercaptopropyl) propionamide,
2-amino N-(5-mercaptopentyl) propionamide,
2-amino N-[(2-mercapto-2'-ethoxy)ethyl] propionamide,
3-amino N-(3-mercaptopropyl) propionamide,
3-amino N-(5-mercaptopentyl) propionamide,
3-amino N-[(2-mercapto-2'-ethoxy) ethyl] propionamide
2-amino N-(2-mercaptoethyl)-3-methyl butanamide,
2-amino N-(2-mercaptoethyl)-4-methyl pentanamide,
α-amino N-(2-mercaptoethyl) hydrocinnamide,
4-amino-5-[(2-mercaptoethyl) amino]-5-oxo pentanoic acid,
4-amino N-(2-mercaptoethyl) butanamide,
4-amino N-(3-mercaptopropyl) butanamide,
6-amino N-(5-mercaptopentyl) butanamide,
4-amino [N-2'-(2-mercaptoethoxy) ethyl] butanamide
6-amino N-(2-mercaptoethyl) hexanamide, and the hydrochlorides thereof.

4. The composition of claim 1 wherein said compound of formula (I) is present in an amount ranging from 2 to 30 percent by weight based on the total weight of said composition.

5. The composition of claim 1 wherein said compound of formula (I) is present in an amount ranging from 5 to 25 percent by weight based on the total weight of said composition.

6. The composition of claim 1 which also contains at least one other reducing agent selected from the group consisting of thioglycolic acid, glycerol monothioglycolate, glycol monothioglycolate, cysteamine, $C_1$-$C_4$ acylated derivative of cysteamine, cysteine, N-acetylcysteine, N-(2-mercaptoethyl) gluconamide, β-mercaptopropionic acid and its derivatives, thiolactic acid, pantethein, thioglycerol, alkali metal sulfite, alkaline earth metal sulfite, alkali metal bisulfite and alkaline earth metal bisulfite.

7. The composition of claim 1 which also includes at least one of a cationic polymer, a softening agent, a protein hydrolyzate, a wax, an opacifying agent, a perfume, a dye, a non-ionic surfactant, a cationic surfactant, an alcohol, a treating agent or a penetration agent.

8. The composition of claim 1 having a pH ranging from 4.5 to 11 obtained with (1) an alkaline agent selected from the group consisting of ammonia, monoethanolamine, diethanolamine, triethanolamine, an alkaline carbonate, an alkaline bicarbonate, ammonium carbonate, ammonium bicarbonate and an alkaline hydroxide, or (2) an acidifying agent selected from the group consisting of hydrochloric acid, acetic acid, lactic acid, oxalic acid and boric acid.

9. The composition of claim 8 having a pH ranging from 6 to 10.

10. The composition of claim 1 wherein said compound of formula (I) is formed in situ starting with the thioester precursor thereof having the formula

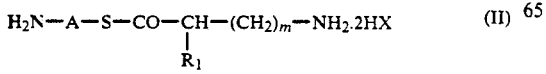

wherein A, $R_1$ and m have the same meanings given in claim 1 and X is Cl or Br.

11. The composition of claim 10 wherein said compound of formula (II) is present in an amount ranging from 2 to 30 percent by weight based on the total weight of said composition.

12. The composition of claim 10 wherein said compound of formula (II) is present in an amount ranging from 5 to 25 percent by weight based on the total weight of said composition.

13. The composition of claim 1 which also contains at least one disulfide, said composition being a self-neutralizing composition.

14. The composition of claim 13 wherein said disulfide is dithioglycolic acid, dithioglycerol, cystamine, N,N'-diacetylcystamine, cystine or panthetin.

15. The composition of claim 13 wherein said disulfide is present in a molar amount ranging from 0.5 to 2.5 relative to the compound of the formula (I).

16. The composition of claim 13 wherein said disulfide is present in a molar amount ranging from 1 to 2 relative to the compound of formula (I).

17. The composition of claim 13 wherein said disulfide has the formula

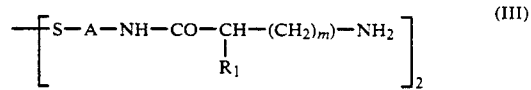

wherein
A represents a divalent radical —$(CH_2)_n$— wherein n is a whole number ranging from 2 to 5, or a divalent radical —$(CH_2)_2$—O—$(CH_2)_2$,
m is 0 or a whole number ranging from 1 to 4,
  (i) when m is 0, $R_1$ represents hydrogen, methyl, ethyl, isopropyl, isobutyl, 2-methyl butyl, benzyl, 4-amino butyl, 3-quanidino propyl, 2-methylthioethyl, carboxymethyl or 2-carboxyethyl and
  (ii) when m is a whole number ranging from 1 to 4, $R_1$ represents hydrogen or lower alkyl having 1-5 carbon atoms.

18. The composition of claim 17 wherein said disulfide of formula (III) is selected from the group consisting of:
N,N'(2,1-dithiodiethanediyl) bis [3-amino propionamide],
N,N'-(2,1-dithiodiethanediyl) bis[2-amino acetamide],
N,N'-(2,1-dithiodiethanediyl) bis[2-amino propionamide],
N,N'-[dithiobis (trimethylene)] bis [2-amino propionamide],
N,N'-(2,1-dithiodiethanediyl) bis [α-amino benzene propionamide],
N,N'-(2,1-dithiodiethanediyl) bis [2-amino-4-methyl pentanamide],
N,N'-(2,1-dithiodiethanediyl) bis [4-amino butanamide],
N,N'-[dithiobis(trimethylene)] bis [3-amino propionamide],
5,5'-[dithiobis (2,1-ethanediylimino)] bis [4-amino-5-oxo pentanoic] acid,
N,N'-[dithiobis (trimethylene)] bis [2-amino acetamide],
N,N'-[dithiobis (pentamethylene)] bis [2-amino acetamide], N,N'-[dithiobis (pentamethylene)] bis [4-amino butanamide], N,N'-[dithiobis (2-ethyloxyethyl)] bis [2-amino acetamide] and N,N'-(2,1-dithiodiethanediyl) bis [6-amino hexanamide].

19. A process for the permanent deformation of hair comprising in a first stage reducing the disulfide bonds of keratin by applying to the hair a reducing composition and in a second stage reforming the said disulfide bonds by applying to the hair an oxidizing composition, said reducing composition being the composition of claim 1.

20. The process of claim 19 wherein said reducing composition is permitted to remain in contact with the hair in said first stage for a period of time ranging from 5 to 60 minutes.

* * * * *